United States Patent [19]

Russo

[11] 4,395,091

[45] Jul. 26, 1983

[54] OPTICAL COUPLING DEVICE FOR USE WITH A PLASMA EMISSION SPECTROMETER

[75] Inventor: Albert J. Russo, Norwalk, Conn.

[73] Assignee: The Perkin-Elmer Corporation, Norwalk, Conn.

[21] Appl. No.: 202,511

[22] Filed: Oct. 31, 1980

[51] Int. Cl.³ .................. G01N 21/73; G02B 5/00
[52] U.S. Cl. .................................... 350/319; 356/316
[58] Field of Search ................... 356/313–316, 356/417; 350/319

[56] References Cited

U.S. PATENT DOCUMENTS

| | | | |
|---|---|---|---|
| 3,645,627 | 2/1972 | Brody et al. | 356/417 X |
| 3,669,546 | 6/1972 | Virloget | 356/313 |
| 4,097,239 | 6/1978 | Patterson | 356/417 X |
| 4,322,165 | 3/1982 | Ellebracht et al. | 356/316 |

OTHER PUBLICATIONS

Kirkbright et al., *Analytica Chimica Acta*, vol. 62, No. 2, Dec. 1972, pp. 241–251.
Ellebracht, "Plasma Atomic Emission Spectroscopic Determination of Sulfur", A Thesis Presented to the Faculty of the Graduate School University of Missouri, Aug. 1977.
Crider: *Analytical Chemistry*, vol. 37, No. 13, Dec. 1965, pp. 1770–1773.
Ohta et al., *Talanta*, vol. 25, No. 3, Mar. 1978, pp. 160–162.

*Primary Examiner*—F. L. Evans
*Attorney, Agent, or Firm*—S. A. Giarratana; F. L. Masselle; R. A. Hays

[57] ABSTRACT

An optical coupling device for providing an oxygen-free optical path between a plasma torch and a monochromator includes a hollow body having means associated therewith for the venting thereof.

9 Claims, 3 Drawing Figures

OPTICAL COUPLING DEVICE FOR USE WITH A PLASMA EMISSION SPECTROMETER

BACKGROUND OF THE INVENTION

The present invention generally relates to analytical instruments employing spectroscopic techniques for measuring a test sample and, in particular, relates to an optical coupling device for use in conjunction with such an instrument.

Many analytical instruments employ spectroscopic techniques in measuring a test sample. The spectroscopic portion of such an instrument is usually positioned between a light radiation source and a detection mechanism and is commonly sealed, or closed, to protect the optical faces from contamination. One such instrument is commonly known as a plasma flame emission spectrometer. In such a spectrometer, a liquid containing a test sample is first atomized and then burned in a plasma torch, such as the torch described in U.S. Pat. No. 3,467,371 issued to Greenfield et al. on Sept. 16, 1969. The plasma torch supplies considerable energy, due to its relatively high temperature, usually on the order of 5,000° Centigrade, to the atoms of the test sample. This energy causes some of the electrons of the atoms to jump from their ground state to a predictable, but unstable, higher energy level state. When such an excited electron decays to the ground state light radiation is emitted. The energy of the light radiation is equal to the quantum energy difference between the ground state and the higher excited state. As well known, this emitted light radiation is characteristic of the atom involved and can be measured to determine information about the presence of a particular element in the test sample. These elemental measurements are well known in the analytical instrument field.

As well known, a plasma torch emission source can invest ground state electrons of some atoms with a sufficient quanta of energy that the resulting wavelength of the subsequent emitted light, due to electron degeneration, is in the ultra-violet region of the light spectrum. For example, light waves having wavelengths less than about 200 nanometers are often emitted in plasma torch emission instruments. However, light radiation of such a rather short wavelength is rapidly attenuated by the oxygen in the atmosphere. In the particular example of a plasma torch flame emission spectrophotometer, the attenuating medium is the air ambient space between the flame of the plasma torch and the optical entrance of a monochromator. Thus one of the more advantageous features of plasma torch emission measurements, i.e., obtaining characteristic spectral lines having comparatively high energy and relatively short wavelength, is severely inhibited by the inherent spacing between the plasma torch and the optical segment of the instrument.

SUMMARY OF THE INVENTION

In view of the foregoing it is therefore a main objective of the present invention to provide an optical coupling device between an emission source and an optical mechanism. The optical coupling device includes a hollow body having an inlet port means associated therewith through which an oxygen-free gas can be introduced thereto to provide an oxygen-free path which permits the transmission of light of short wavelength therethrough.

Another object of the present invention is to provide an optical coupling device having a substantially oxygen free optical path therethrough.

These and other objects will become apparent from the following drawing and specification.

DETAILED DESCRIPTION OF THE INVENTION

Figure 1:
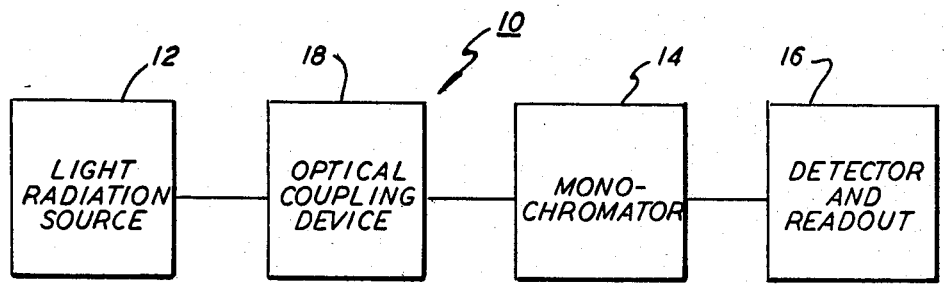
FIG. 1 is a block diagram of the primary components of a typical analytical instrument but which includes a device embodying the principles of the present invvention.

The primary components of a typical analytical instrument, for example a plasma flame emission spectrometer, are indicated generally at 10 in FIG. 1. The plasma flame emission spectrometer 10 includes a light radiation source 12, a monochromator 14 and a detector/readout apparatus 16. In addition, and in accordance with the principles of the present invention, the plasma flame emission spectrometer 10 includes an optical coupling device 18 more fully described below. The source 12 can be, for example, a plasma torch, such torches are known in the art and are designed to impart thermal energy to the atoms of a test sample which is atomized and injected thereinto. The monochromator 14 is, as well known in the art, an optical apparatus for isolating a relatively narrow spectral portion of the light spectrum impinging on its entrance port. The isolated spectral portion is then projected onto an optical detecting/readout apparatus 16 which is provided in a conventional fashion. These three components are so well known in the art that further detailed discussion thereof is believed to be unnecessary. The optical coupling device 18 shown in FIG. 1 preferably is adapted to provide the only optical path between the plasma torch, the source 12 and the monochromator 14.

Figure 2:
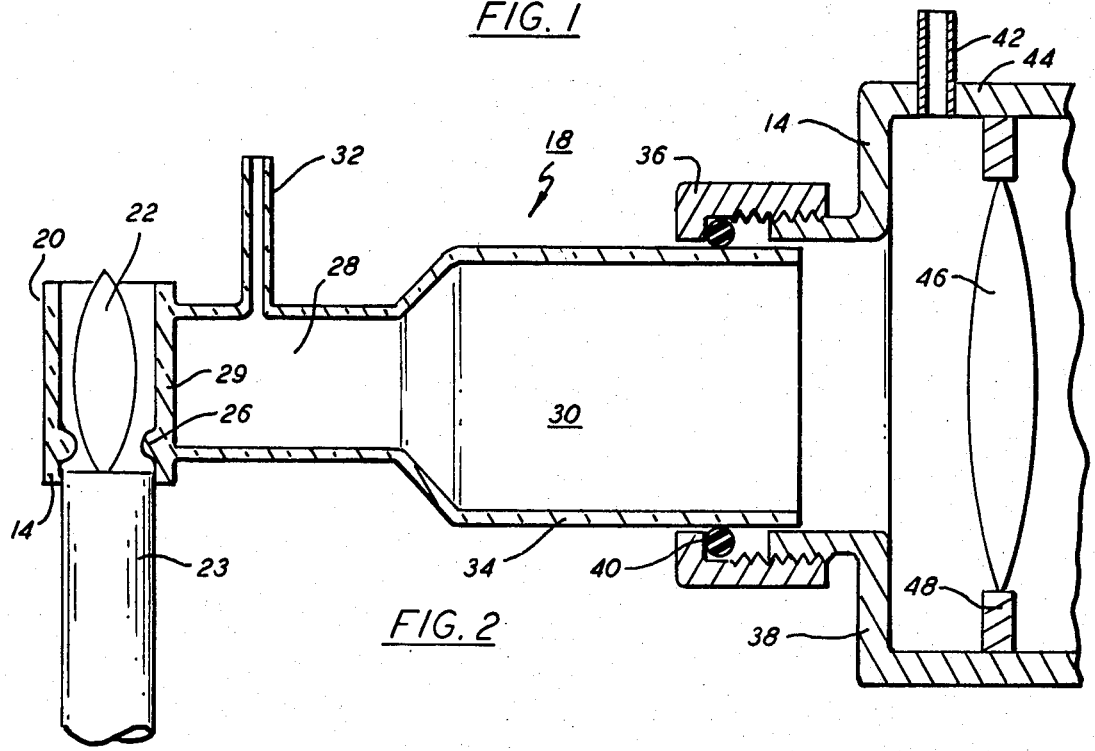
FIG. 2 is a cross-sectional view of one embodiment of an optical coupling device, not drawn to scale, employing the principles of the present invention.

In one embodiment, for example, as shown in FIG. 2, the optical coupling device 18 includes a hollow tube 20 i.e., an empty tube, which is open at both ends thereof and dimensioned so as to fit over and surround the flame 22 of a plasma torch 23. Preferably the lower end 24 of the hollow tube 20 is provided with a shoulder 26 dimensionally adapted to mate with the plasma torch 23. A first segment 28 of a hollow body 30 i.e., an empty body, is rigidly affixed to and extends from the hollow tube 20 of the optical coupling device 18. Preferably, although not necessarily, the first segment 28 is a hollow cylindrical segment adapted and shaped so as to mate, in a gaseously sealed fashion, with one side 29 of the hollow tube 20. In the preferred embodiment, the first segment 28 mates with the hollow tube 20 at a point such that the linear axis of the body 30 is substantially central to the flame of the plasma torch 23. This alignment ensures that the emitted light radiation of interest is at its highest intensity along the axis of the body 30. As shown in FIG. 2, an exit, or purge, port 32 extends from the first segment 28 and, as more fully discussed below, serves as a vent to the ambient atmosphere.

The body 30 of the optical coupling device 18 also includes a second cylindrical segment 34 which is preferably axially aligned with the first segment 28. The diameter of the second segment 34 should be at least as large as that of the first segment 28.

The optical coupling device 18 is affixed to the monochromator 14 in such a fashion that a gaseous seal is formed at the interface therebetween. In one embodiment the gaseous seal is accomplished by a threaded connection between a first, internally threaded, flange 36 surrounding the second segment 34 and a second, externally threaded, flange 38 projecting from the monochromator 14. An O-ring 40 is located around the second segment 34 so that when the first and second flanges, 36 and 38 respectively, are threaded one onto the other, the pressure thus generated deforms the O-ring 40 to produce a gaseous seal.

In this embodiment, the monochromator 14 is provided with an inlet port 42 through one wall 44 thereof. The inlet port 42 is situated such that it is between the second flange 38 and the first optical element 46 of the monochromator 14. As shown, the monochromator 14 is substantially gaseously sealed with respect to the inlet port 42 by the mounting means 48 associated with the first optical element 46. Alternatively, if the monochromator 14 itself is sufficiently sealed then it and the device 18 can have a common ambient.

Thus, in operation, an oxygen-free inert gas is injected, via the inlet port 42, into the optical coupling device 18 to drive out, via the vent port 32, any oxygen containing ambient therein.

The optical coupling device 18 is preferably made of quartz although any other optically transparent material capable of withstanding temperatures on the order of about 5,000° Centigrade can also be used.

Figure 3:
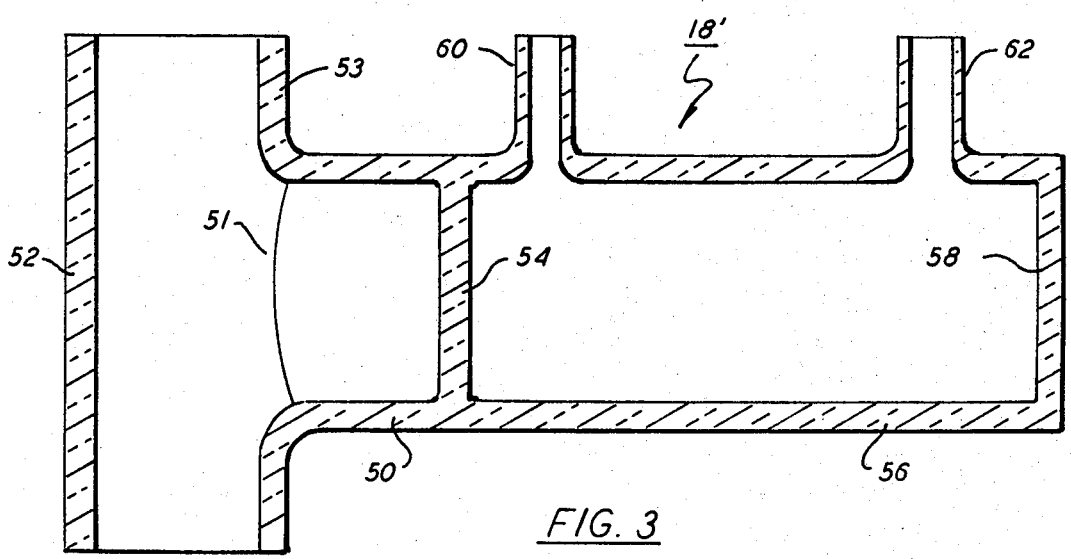
FIG. 3 is a cross-sectional view of another embodiment of an optical coupling device, not drawn to scale, employing the principles of the present invention.

Referring now to FIG. 3, there is shown another embodiment of an optical coupling device 18' wherein a first cylindrical segment 50 is rigidly affixed about an opening 51 in the wall 53 of a hollow tube 52. The first segment 50 includes a quartz window 54 recessed a distance from the tube 52. The recessed window 54, being recessed from the tube 52, extends the lifetime of the optical coupling device 18' by reducing the heat to which the recessed window 54 is subjected. Nevertheless, the window 54 is designed such that it seals that portion of the first segment 50 between the tube 52 and a monochromator not shown in FIG. 3. In addition, the portion of the first segment 50 between the recessed window 54 and the flame is nevertheless maintained oxygen-free due to the presence of an argon gaseous "seal" which usually surrounds conventional plasma torches during the operation thereof.

The optical coupling device 18' shown in FIG. 3 includes a second segment 56 having a sealed rear window 58 proximate the end thereof.

The first segment 50 includes a first means 60 in gaseous communication therewith and the second segment 56 includes a second means 62 for providing gaseous communication therewith. The first and second means, 60 and 62, can be interchangably used as input and venting ports. In this embodiment the optical coupling device 18' can be sealed after it is filled with an oxygen-free inert gas, such as, for example, nitrogen.

It will be understood that instead of filling the device, 18 or 18', with an inert oxygen-free gas to provide an oxygen-free optical path therethrough, the device 18 or 18' may just be evacuated using a known vacuum system. In such an embodiment, one of the ports, i.e. either 32 or 42 of the device 18 shown in FIG. 2, is sealed and a vacuum is drawn via the other port, i.e. either 42 or 32. Specifically, a vacuum of about $10^5$ torr would be sufficient to provide the desired substantially oxygen-free path. In such an instance the venting occurs due to the reduced pressure at the port used which thereby causes the oxygen containing ambient within the body 30 to exit the body via that port.

While the above description is specifically directed toward the use of the present invention in a plasma flame emission spectrometer, such use and such limitations thereon are exemplary only as the principles of the present invention are generally applicable to other similar devices. Thus the scope and use of the present invention is limited only by the appended claims and the reasonable interpretation thereof.

What is claimed is:

1. An optical coupling device for use with a plasma emission spectrometer comprising:
    a hollow optically transparent high temperature body, said body having a first segment and a second segment, said first and said second segments being axially aligned and affixed to each other;
    means for gaseously sealing the end portions of said body;
    means for venting said body whereby said device provides an oxygen-free optical path along said body; and
    a hollow optically transparent high temperature tube integral with said first segment at the end thereof distal from said second segment, said tube being adapted to surround a plasma torch and align said body therewith.

2. A device as claimed in claim 1 further including inlet means through which an oxygen-free gas can be introduced into said body.

3. A device as claimed in claim 1 wherein said hollow tube is perpendicular to the axis of said body.

4. A device as claimed in claim 1 wherein said means for gaseously sealing said body includes an optically transparent window in said first segment, said window being recessed from said hollow tube.

5. A device as claimed in claim 2 wherein said inlet means is intimately affixed to said second segment and said venting means is intimately affixed to said first segment.

6. A device as claimed in claim 5 wherein said body contains an oxygen-free gas and said inlet and venting means are sealed.

7. A device as claimed in claim 1 wherein said body is affixed in gaseously sealed manner to an optical system via said second segment.

8. A device as claimed in claim 7 wherein said gaseous seal is produced via an O-ring.

9. A device as claimed in claim 1 wherein said means for venting evacuates said body.

* * * * *